United States Patent
Wong

(10) Patent No.: US 9,161,606 B1
(45) Date of Patent: Oct. 20, 2015

(54) MAKEUP APPLICATION COMPONENT

(71) Applicant: Zong Jing Investment, Inc., Taipei (TW)

(72) Inventor: Charlene Hsueh-Ling Wong, Taipei (TW)

(73) Assignee: ZONG JING INVESTMENT, INC., Taipei (TW)

( * ) Notice: Subject to any disclaimer, the term of this patent is extended or adjusted under 35 U.S.C. 154(b) by 0 days.

(21) Appl. No.: 14/475,721

(22) Filed: Sep. 3, 2014

(30) Foreign Application Priority Data

Jul. 4, 2014 (TW) .............................. 103123116 A

(51) Int. Cl.
*A45D 44/00* (2006.01)
*A45D 40/30* (2006.01)
*A61K 8/02* (2006.01)
*A45D 33/38* (2006.01)

(52) U.S. Cl.
CPC .............. *A45D 40/30* (2013.01); *A45D 44/002* (2013.01); *A61K 8/02* (2013.01); *A45D 33/38* (2013.01)

(58) Field of Classification Search
CPC ....... A61K 8/02; A61K 8/0212; A61M 35/00; A61M 35/03; A61M 35/003; A45D 44/002; A45D 44/005; A45D 44/22; A45D 40/30; A45D 33/38; A61F 13/122; A61F 2007/0003; A41D 13/11; A41D 13/1107; A41G 7/00; A41G 7/02; B41J 2/0057; B41F 15/0872; B41F 15/0877; B41F 15/0881; B41F 15/0886; B41F 15/089; B41F 15/0895; B41F 17/002; B41F 17/006; B41F 17/28; B41F 17/30; B41F 19/002; B41P 2217/53

USPC ................... 132/333, 200, 319, 320; 446/27; 434/99, 270, 377; 128/857; 604/303, 604/304, 308, 309; 2/9, 173, 206, 11; 428/542.2, 914; 427/1, 2.31, 202, 427/208.8; 401/6; 601/17; 901/43, 50
See application file for complete search history.

(56) References Cited

U.S. PATENT DOCUMENTS

| | | | | |
|---|---|---|---|---|
| 4,117,837 A * | 10/1978 | Masso Remiro | ......... | 606/204.35 |
| 4,585,797 A * | 4/1986 | Cioca | ............. | 514/773 |
| 4,591,501 A * | 5/1986 | Cioca | ............. | 424/401 |
| 4,631,227 A * | 12/1986 | Nakamura | ............ | 428/40.1 |
| 5,078,160 A * | 1/1992 | Carbonnier | ............ | 132/320 |
| 6,316,021 B1 * | 11/2001 | Gueret | ............ | 424/443 |
| 6,702,792 B2 * | 3/2004 | Nakamura et al. | ........... | 604/303 |
| 6,730,317 B2 * | 5/2004 | Gueret | ............ | 424/443 |
| 6,793,999 B2 * | 9/2004 | Wittmeyer, Jr. | ............. | 428/40.1 |
| 7,419,677 B2 * | 9/2008 | Gueret | ............ | 424/400 |
| 7,927,680 B2 * | 4/2011 | Marshall | ............ | 428/40.1 |
| 8,254,637 B2 * | 8/2012 | Abourizk et al. | ............ | 382/106 |
| 8,262,303 B2 * | 9/2012 | Burnett | ............ | 401/6 |
| 8,358,348 B2 * | 1/2013 | Mohammadi et al. | ...... | 348/207.1 |
| 8,425,477 B2 * | 4/2013 | Mou et al. | ............ | 604/304 |
| 8,491,926 B2 * | 7/2013 | Mohammadi et al. | ........ | 424/443 |

(Continued)

*Primary Examiner* — Vanitha Elgart
(74) *Attorney, Agent, or Firm* — McClure, Qualey & Rodack, LLP

(57) ABSTRACT

A makeup application component includes a three-dimensional mask, a transfer layer, and a pigment layer. A surface curve of a first surface of the three-dimensional mask is corresponding to a surface curve of a face of a user. The transfer layer covers the first surface of the three-dimensional mask. The transfer layer is provided with a first surface and a second surface that are opposite each other. The first surface of the transfer layer clings to the first surface of the three-dimensional mask, and the pigment layer is attached to the second surface of the transfer layer.

7 Claims, 8 Drawing Sheets

(56) References Cited

U.S. PATENT DOCUMENTS

| | | | |
|---|---|---|---|
| 8,540,445 B2* | 9/2013 | Omoto | 401/6 |
| 8,597,667 B2* | 12/2013 | Mou et al. | 424/401 |
| 8,926,391 B2* | 1/2015 | Rodriguez | 446/27 |
| 2004/0091663 A1* | 5/2004 | Jang | 428/68 |
| 2006/0048278 A1* | 3/2006 | Pitsolis | 2/206 |
| 2006/0098076 A1* | 5/2006 | Liang | 347/129 |
| 2008/0014231 A1* | 1/2008 | Okano | 424/401 |
| 2008/0029121 A1* | 2/2008 | Gueret et al. | 132/320 |
| 2008/0051860 A1* | 2/2008 | Wyk | 607/109 |
| 2008/0053476 A1* | 3/2008 | LaHood et al. | 132/320 |
| 2009/0241242 A1* | 10/2009 | Beatty et al. | 2/206 |
| 2010/0228204 A1* | 9/2010 | Beatty et al. | 604/303 |
| 2010/0324509 A1* | 12/2010 | Lee | 604/303 |
| 2012/0012133 A1* | 1/2012 | Riscica | 132/319 |
| 2012/0192884 A1* | 8/2012 | Nasu et al. | 132/200 |
| 2012/0211022 A1* | 8/2012 | Nakamura | 132/319 |
| 2014/0163445 A1* | 6/2014 | Pallari et al. | 602/43 |
| 2014/0290684 A1* | 10/2014 | Samain et al. | 132/200 |
| 2014/0318565 A1* | 10/2014 | Ito et al. | 132/200 |
| 2014/0352031 A1* | 12/2014 | Choi et al. | 2/173 |

* cited by examiner

MAKEUP APPLICATION COMPONENT

CROSS-REFERENCES TO RELATED APPLICATIONS

This non-provisional application claims priority under 35 U.S.C. §119(a) on Patent Application No. 103123116 filed in Taiwan, R.O.C. on 2014 Jul. 4, the entire contents of which are hereby incorporated by reference.

BACKGROUND

1. Technical Field

The present invention relates to makeup application technologies, and in particular, to a makeup application component.

2. Related Art

Love of beauty is human nature. Therefore, manufacturers launch all kinds of cosmetics on the market for consumers to choose from. However, because makeup application techniques of consumers are on different proficiency levels and there are various types of cosmetics, actual makeup application effects usually fall short of expectations of the consumers.

With the continuous evolution of information science and technology, recently, users can practice makeup application skills or present a virtual makeup application effect by using a cosmetics-simulation apparatus. However, according to a simulated makeup application effect on a screen of the simulation apparatus, the user still needs to manually apply cosmetics to a human face by manually-makeup skills. Moreover, an manually makeup application effect on the human face cannot be the same as the simulated makeup application effect on the screen.

Therefore, if the cosmetics are applied by an automatic cosmetics device under automatic control, the cosmetics can be accurately applied to the human face based on the simulated makeup application effect on the screen. However, in terms of designing an automatic cosmetics device, how to implement secure positioning of a makeup tool so as not to hurt the user is always discussed by the related researchers.

SUMMARY

In an embodiment, a makeup application component includes a three-dimensional mask, a transfer layer, and a pigment layer. A surface curve of a first surface of the three-dimensional mask is corresponding to a surface curve of a face of a user. The transfer layer covers the first surface of the three-dimensional mask. The transfer layer is provided with a first surface and a second surface that are opposite each other. The first surface of the transfer layer clings to the first surface of the three-dimensional mask, and the pigment layer is attached to the second surface of the transfer layer.

In some embodiments, the makeup application component may further include a cosmetics machine. The cosmetics machine is used for applying at least one makeup product to the second surface of the transfer layer, to form, on the second surface of the transfer layer, the pigment layer having a pre-determined pattern.

In conclusion, the makeup application component according to the present invention provides a user with a simple, quick, and secure manner for applying makeup. In this embodiment, the three-dimensional mask is a customized mask made according to a face shape of a user, and therefore a curve of the three-dimensional mask is corresponding to the face of the user, so as to provide accurate positioning. Besides, the pigment layer which is already painted on a corresponding position and has a pre-determined pattern is transferred to the face of the user in a transfer manner, so as to quickly apply makeup. Moreover, in the makeup application component according to the present invention, the cosmetics machine can be used to apply the pigment layer having the pre-determined pattern and form the pigment layer on the transfer layer on an inner side of the three-dimensional mask, so as to accurately and conveniently paint a cosmetics pattern desired by the user.

BRIEF DESCRIPTION OF THE DRAWINGS

The present invention will become more fully understood from the detailed description given herein below for illustration only, and thus are not limitative of the present invention, and wherein.

DETAILED DESCRIPTION

Figure 1:
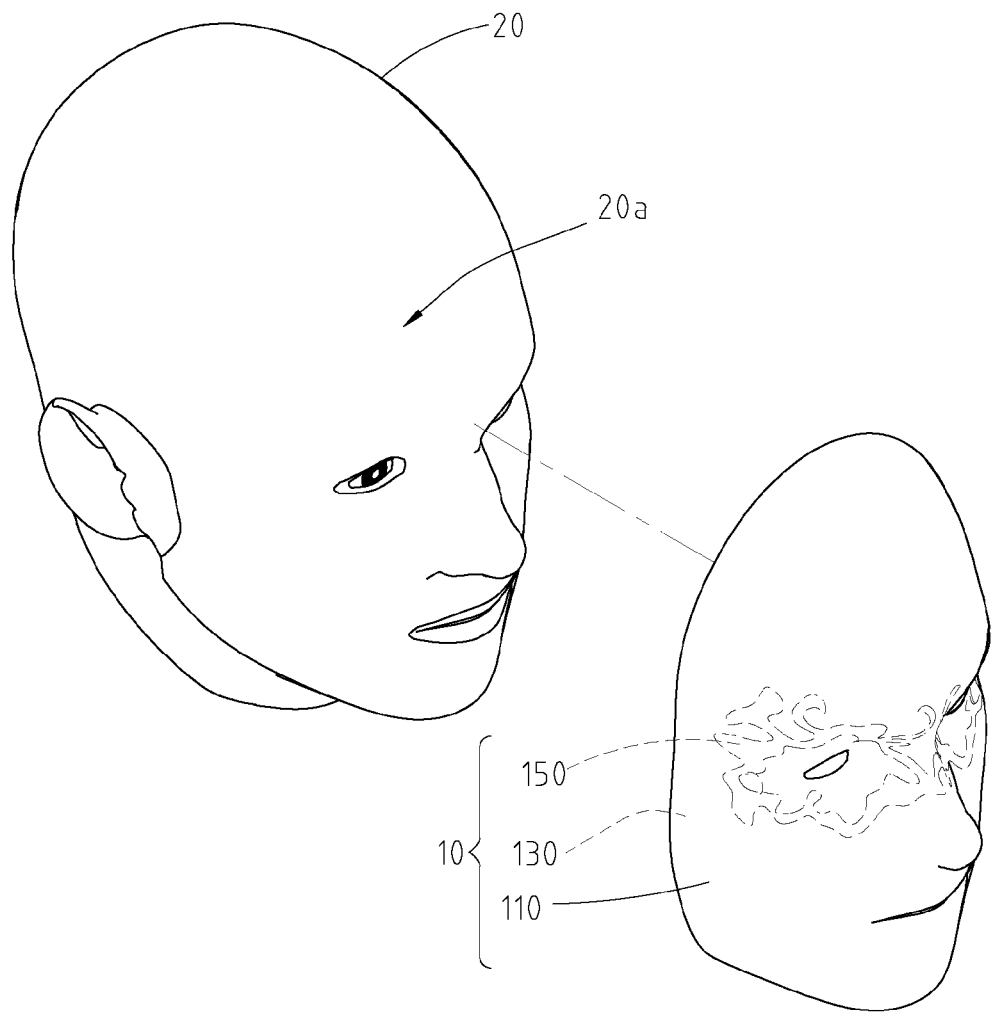
FIG. 1 is a schematic three-dimensional view of a makeup application component according to an embodiment of the present invention.
Figure 2:
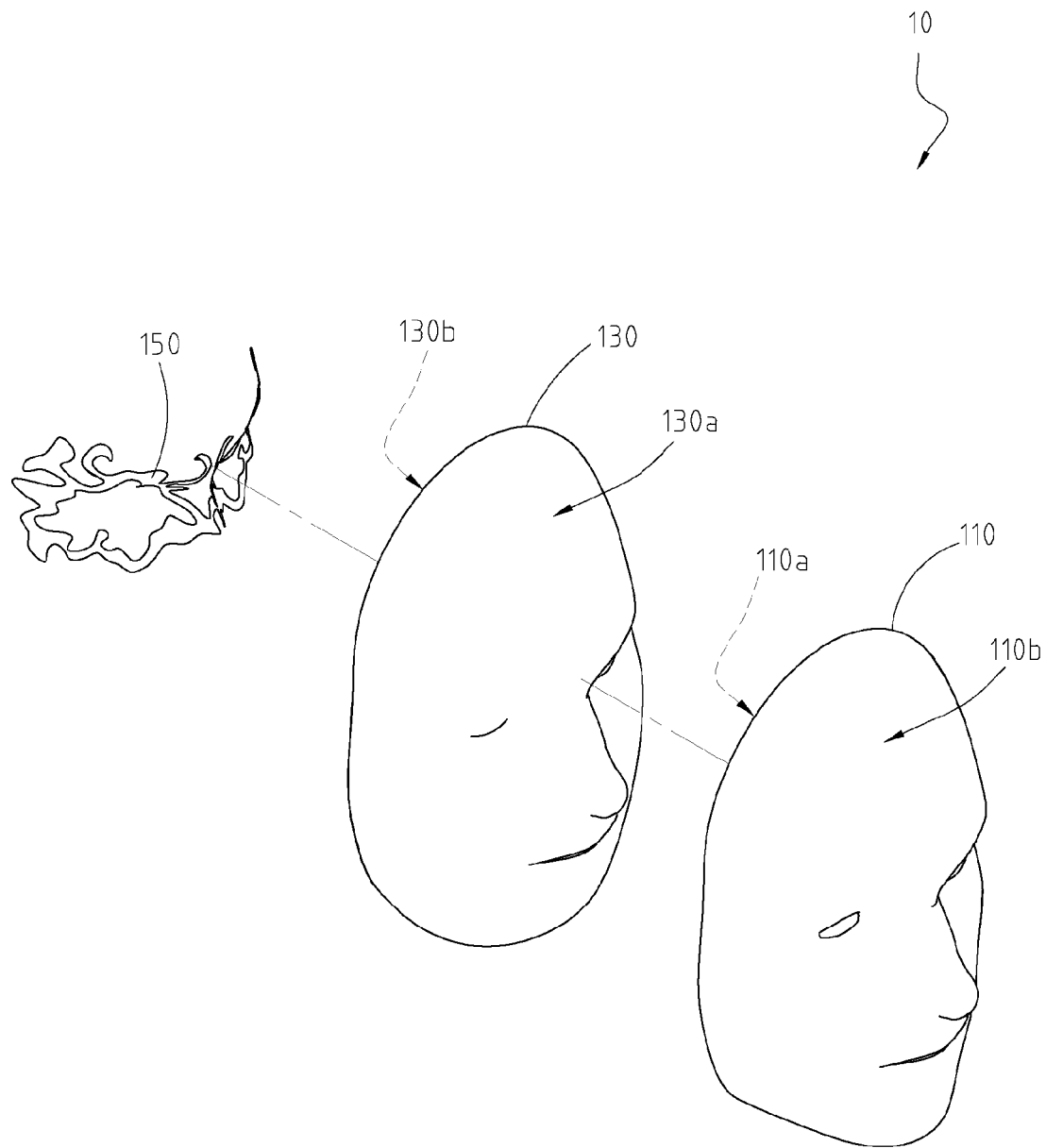
FIG. 2 is a schematic exploded view of a makeup application mask in FIG. 1.
Figure 3:
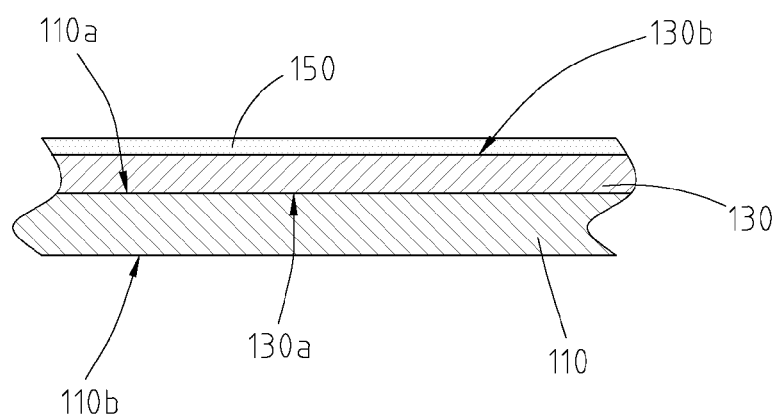
FIG. 3 is a schematic sectional view of the makeup application mask in FIG. 1.

FIG. 1 is a schematic three-dimensional view of a makeup application mask according to an embodiment of the present invention. FIG. 2 is a schematic exploded view of the makeup application mask in FIG. 1. FIG. 3 is a schematic sectional view of the makeup application mask in FIG. 1.

Referring to FIG. 1 to FIG. 3, a makeup application component includes a makeup application mask 10, and the makeup application mask 10 includes a three-dimensional mask 110, a transfer layer 130, and a pigment layer 150. The three-dimensional mask 110, the transfer layer 130, and the pigment layer 150 overlap each other in order. In other words, the transfer layer 130 covers a first surface 110a of the three-dimensional mask 110. The transfer layer 130 is provided with a first surface 130a and a second surface 130b that are opposite each other. The first surface 130a of the transfer layer 130 clings to the first surface 110a of the three-dimensional mask 110, and the pigment layer 150 is attached to the second surface 130b of the transfer layer 130.

In this embodiment, a surface curve of the first surface 110a of the three-dimensional mask 110 is corresponding to a surface curve of a face 20a of a user 20. In other words, when the user 20 covers the face 20a with the three-dimensional mask 110, the first surface 110a of the three-dimensional mask 110 clings to the face 20a of the user 20. In this embodiment, a shape of the three-dimensional mask 110 may be printed according to the surface curve of the face 20a of the user 20 by using a 3D printer. Besides, the three-dimensional mask 110 may be produced according to the surface curve of the face 20a of the user 20 by using a molding technology such as mould molding, injection molding, extrusion, rolling, hot press molding, mould injection molding, compression molding, or foam molding. In this embodiment, the three-dimensional mask 110 may be made of synthetic rubber, such as silica gel or polyurethane (PU) rubber.

Figure 4:
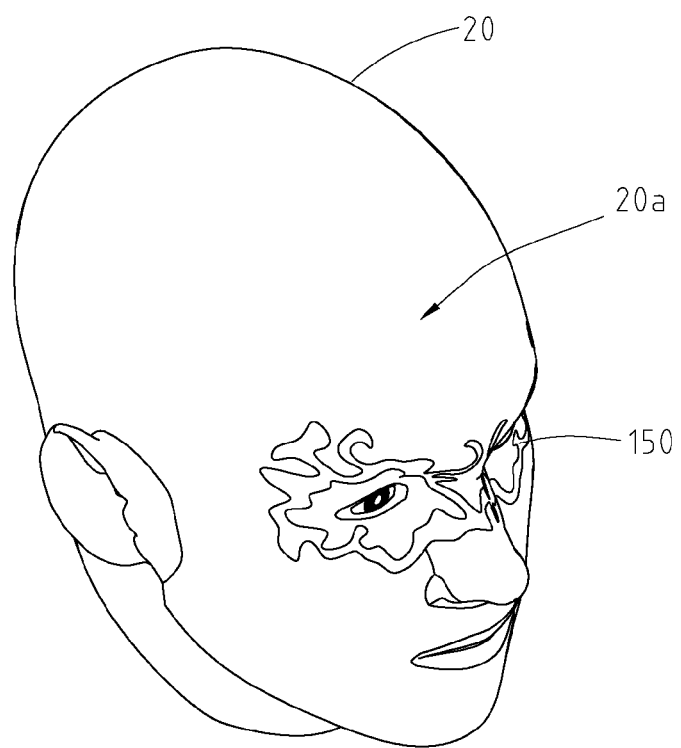
FIG. 4 is a schematic view of a user using the makeup application mask in FIG. 1.

Adhesion between the transfer layer 130 and the three-dimensional mask 110 is greater than adhesion between the pigment layer 150 and the transfer layer 130. The pigment layer 150 has a pattern (referred to as a predetermined pattern in the following) which the user 20 intends to paint on the face 20a, and a position of the pigment layer 150 on the second surface 130b of the transfer layer 130 is corresponding to a position, on which the user 20 intends to paint the pattern, on the face 20a. That is, when the user 20 covers the face 20a with the three-dimensional mask 110 and presses the second surface 110b of the three-dimensional mask 110 against the face 20a of the user 20, the pigment layer 150 is separated from the transfer layer 130 and transferred to the corresponding position on the face 20a of the user 20, as shown in FIG. 4.

In some embodiments, the transfer layer 130 may be secured on the three-dimensional mask 110. In this embodiment, the transfer layer 130 may be formed by spraying a transfer material on the entire first surface 110a of the three-dimensional mask 110, and when the transfer material is hardened, the transfer layer 130 is formed.

In some embodiments, the transfer layer 130 may be bonded to the three-dimensional mask 110.

Figure 5:
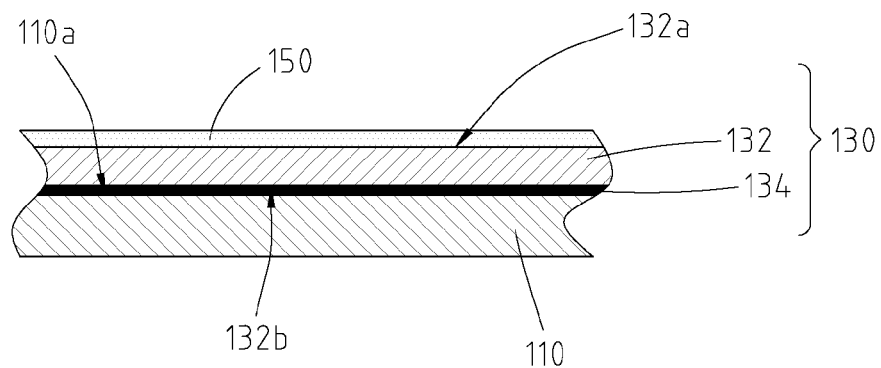
FIG. 5 is a schematic sectional view of an embodiment of the makeup application mask.

In an embodiment, referring to FIG. 5, the transfer layer 130 may include a facial mask 132 and an adhesive layer 134. In this case, the three-dimensional mask 110, the adhesive layer 134, the facial mask 132, and the pigment layer 150 overlap each other in order. In this embodiment, the pigment layer 150 is attached to one surface 132a of the facial mask 132. The adhesive layer 134 is located between the three-dimensional mask 110 and the facial mask 132, and is used for bonding another surface 132b of the facial mask 132 and the first surface 110a of the three-dimensional mask 110. Adhesion of the adhesive layer 134 is greater than adhesion between the pigment layer 150 and the facial mask 132.

In this embodiment, the facial mask 132 may be made of non-woven fabric, wood pulp silk, cotton nature fiber fabric, biological fiber, cellulosic fiber, or the like. The non-woven fabric is also referred to as water jet fabric. The non-woven fabric is made of cotton and polyester compound with the content of the cotton being 10% to 50%. A non-woven fabric facial mask is soft, tough, and thick, and does not break easily. The wood pulp silk may be made of 100% natural wood pulp. A water holding capacity of a wood pulp silk facial mask is 1.5 to 2.5 times greater than that of the non-woven fabric facial mask. The wood pulp silk facial mask is soft with a good clinging property, and does not cause skin allergy easily. The cotton nature fiber fabric facial mask is soft with an excellent clinging property. The biological fiber is micro-biological fiber produced by naturally fermenting pure plant fiber organic ingredients with a selected culture. The biological fiber includes more than 99.9% cellulose. A biological fiber facial mask is soft, biodegradable, 100% biocompatible, and skin-friendly, and has great heat resistance and air permeability.

The adhesive layer 134 may be made of a weak-adhesion pressure-sensitive hot-melt adhesive, a non-setting adhesive, a waterborne PU adhesive, or the like. The weak-adhesion pressure-sensitive hot-melt adhesive has features such as weak adhesion, non-transferability, and good cohesion. The non-setting adhesive is also referred to as a self-adhesive label material, and is a compound material, where a paper, a thin film, or a special material is used as a surface material, the back of the paper, the thin film, or the special material is coated with an adhesive, and a silicon-coated protective paper is used as a bottom paper. The waterborne PU adhesive is an adhesive resembling waterborne polyurethane among waterborne adhesives, and is a new polyurethane system in which water replaces an organic solvent and is used as a dispersion medium. The waterborne PU adhesive is also referred to as water-dispersed polyurethane, water-system polyurethane, or water-based polyurethane. The waterborne PU adhesive is pollution-free and secure with good mechanical properties and compatibility, and can be modified easily.

In terms of manufacturing the makeup application mask 10, any one of corresponding materials in the foregoing may be used to manufacture the three-dimensional mask 110, the adhesive layer 134, or the facial mask 132.

Figure 6:
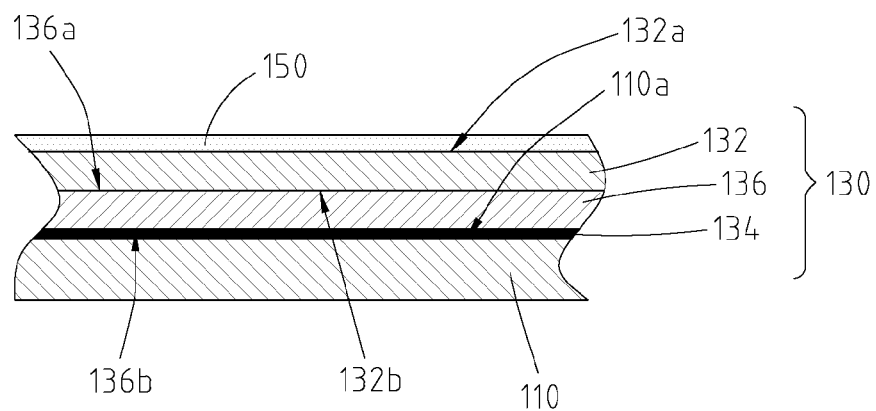
FIG. 6 is a schematic sectional view of another embodiment of the makeup application mask.

In an embodiment, referring to FIG. 6, a backing 136 may be designed for the transfer layer 130 to support the facial mask 132. In other words, the transfer layer 130 may include the facial mask 132, the adhesive layer 134, and the backing 136, and the three-dimensional mask 110, the adhesive layer 134, the backing 136, the facial mask 132, and the pigment layer 150 overlap each other in order. In this embodiment, the pigment layer 150 is attached to one surface 132a of the facial mask 132. The backing 136 is secured on another surface 132b of the facial mask 132. In this embodiment, one surface 136a of the backing 136 clings to the another surface 132b of the facial mask 132. The adhesive layer 134 is located between the three-dimensional mask 110 and the backing 136, and is used for bonding the another surface 136b of the backing 136 and the first surface 110a of the three-dimensional mask 110. Adhesion of the adhesive layer 134 is greater than adhesion between the pigment layer 150 and the facial mask 132. In this embodiment, the backing 136 may be made of a pearl film or a polypropylene (PP) cloth film.

In terms of manufacturing the makeup application mask 10, any one of corresponding materials in the foregoing may be used to manufacture the three-dimensional mask 110, the adhesive layer 134, the backing 136, or the facial mask 132.

In some embodiments, the transfer layer 130 may removably cling to the first surface 110a of the three-dimensional mask 110. Therefore, after the pigment layer 150 is separated from the transfer layer 130 and transferred to the corresponding position on the face 20a of the user 20, the user 20 can remove the transfer layer 130 from the first surface 110a of the three-dimensional mask 110, and apply a new transfer layer 130 to the first surface 110a of the three-dimensional mask 110 during next use.

Figure 7:
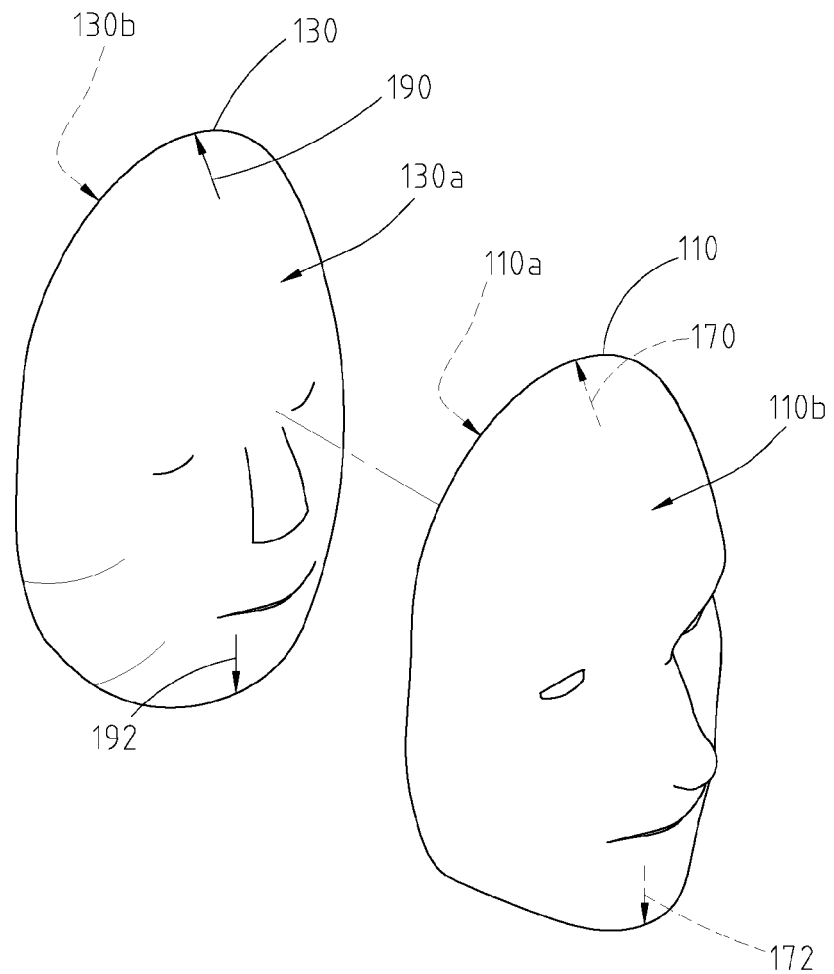
FIG. 7 is a schematic exploded view of a makeup application component according to another embodiment of the present invention.

In some embodiments, referring to FIG. 7, the makeup application mask 10 may further include multiple first marks 170 and 172 and multiple second marks 190 and 192.

The first marks 170 and 172 are separately disposed on different positions on the first surface 110a of the three-dimensional mask 110. The second marks 190 and 192 are separately disposed on different positions on the first surface 130a, which faces the first surface 110a of the three-dimensional mask 110, of the transfer layer 130 (that is, the another surface 132b of the facial mask 132 or the another surface 136b of the backing 136). A position of the first mark 170 on the three-dimensional mask 110 is corresponding to a position of the second mark 190 on the transfer layer 130 (the facial mask 132 or the backing 136), and a position of the first mark 172 on the three-dimensional mask 110 is corresponding to a position of the second mark 192 on the transfer layer 130 (the facial mask 132 or the backing 136).

Therefore, when the user 20 bonds the transfer layer 130 to the first surface 110a of the three-dimensional mask 110, the user 20 may first bond the corresponding first marks and second marks, and then smoothly press other parts of the transfer layer 130 against the first surface 110a of the three-dimensional mask 110, so that the three-dimensional mask 110 and the transfer layer 130 cling together in correct positions.

Figure 8:
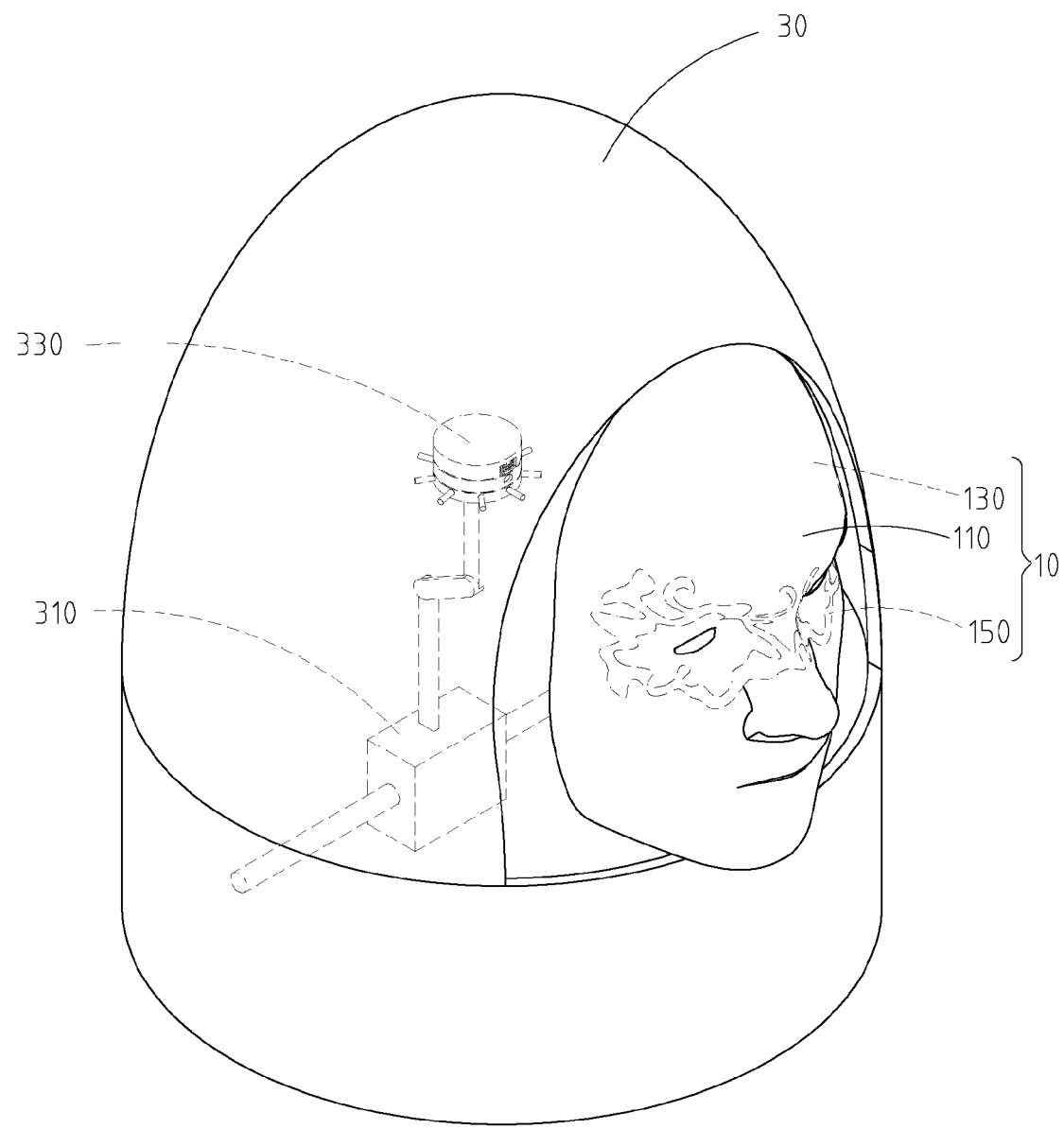
FIG. 8 is a schematic three-dimensional view of a makeup application component according to still another embodiment of the present invention.
Figure 9:
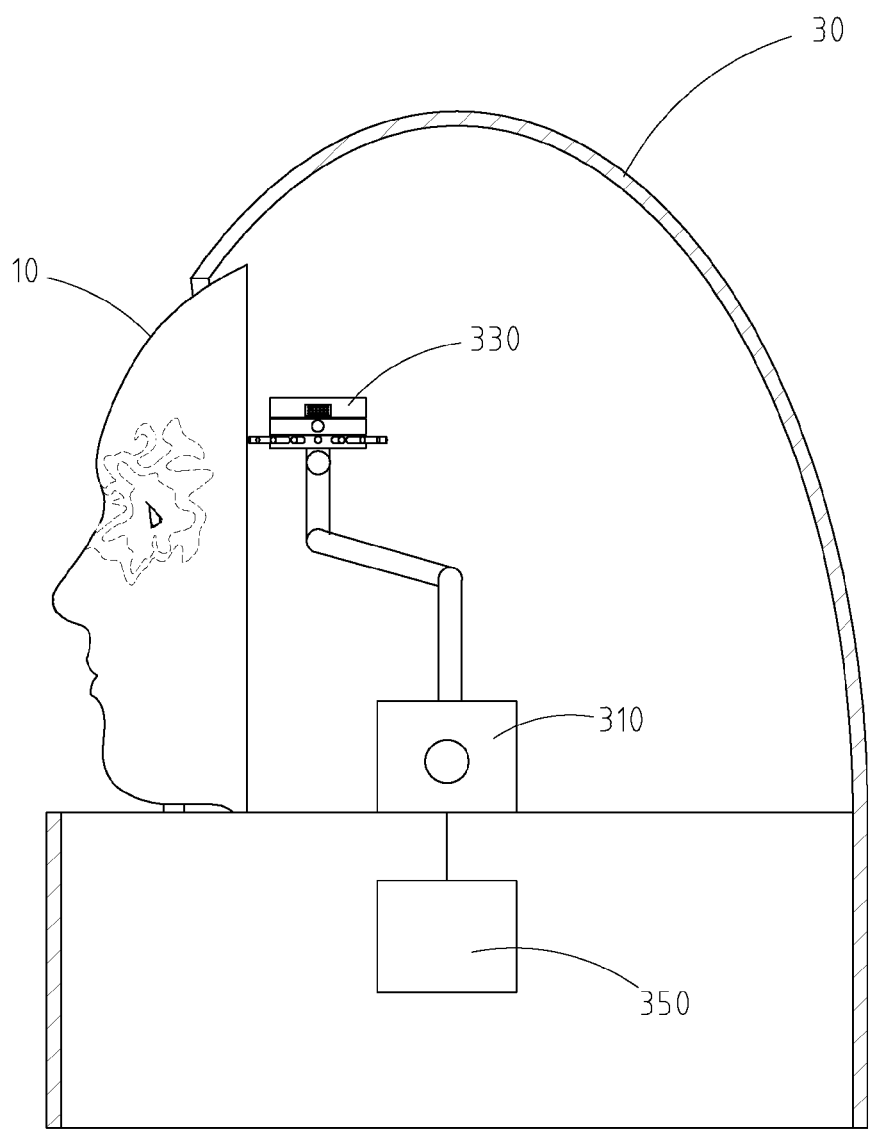
FIG. 9 is a schematic sectional view of the makeup application component in FIG. 8.

In some embodiments, referring to FIG. 8 and FIG. 9, the makeup application component may further include a cosmetics machine 30. The cosmetics machine 30 includes a three-dimensional mobile component 310, a coloring component 330, and a control component 350. The control component 350 is electrically connected to the three-dimensional mobile component 310 and the coloring component 330. The control component 350 may be implemented by a processing unit in cooperation with a storage unit. The processing unit may be a microprocessor, a microcontroller, a digital signal processor, a microcomputer, a central processing unit, a field programmable gate array, a programmable logic device, a state machine, a logic circuit, an analog circuit, a digital circuit, and/or any other device operating a signal (analog and/or digital) based on an operating instruction. The storage unit may be a read-only memory, a random access memory, a non-permanent memory, a permanent memory, a static memory, a volatile memory, a flash memory, and/or any other device storing digital information.

The control component 350 may obtain, according to a colored pattern, multiple multi-dimensional coordinate instructions and multiple coloring instructions corresponding to these multi-dimensional coordinate instructions. The control component 350 may control movement of the multi-dimensional mobile component 310 according to the multi-dimensional coordinate instructions. After the multi-dimensional mobile component 310 moves according to the multi-dimensional coordinate instructions and drives the coloring component 330 to move to a fixed position, the control component 350 then controls, according to the corresponding coloring instructions, the coloring component 330 to apply at least one makeup product to the second surface 130b (that is, the surface 132a of the facial mask 132) of the transfer layer 130. After all the multi-dimensional coordinate instructions and coloring instructions corresponding to the colored pattern are executed, all makeup products applied to the second surface 130b of the transfer layer 130 are distributed in a pre-determined pattern, that is, the makeup products form a pigment layer 150 having the pre-determined pattern.

In conclusion, the makeup application component according to the present invention provides a user with a simple, quick, and secure manner for applying makeup. In this embodiment, the three-dimensional mask is a customized mask made according to a face shape of a user, and therefore a curve of the three-dimensional mask is corresponding to the face of the user, so as to provide accurate positioning. Besides, a pigment layer which is already painted on a corresponding position and has a pre-determined pattern is transferred to the face of the user in a transfer manner, so as to quickly apply makeup. Moreover, in the makeup application component according to the present invention, the cosmetics machine can be used to apply the pigment layer having the pre-determined pattern and form the pigment layer on the transfer layer on an inner side of the three-dimensional mask, so as to accurately and conveniently paint a cosmetics pattern desired by the user.

While the disclosure has been described by the way of example and in terms of the preferred embodiments, it is to be understood that the invention need not be limited to the disclosed embodiments. On the contrary, it is intended to cover various modifications and similar arrangements included within the spirit and scope of the appended claims, the scope of which should be accorded the broadest interpretation so as to encompass all such modifications and similar structures.

What is claimed is:

1. A makeup application component, comprising:
    a three-dimensional mask, wherein a surface curve of a first surface of the three-dimensional mask is corresponding to a surface curve of a face of a user;
    a transfer layer, removably clinging to and covering the first surface of the three-dimensional mask, wherein the transfer layer is provided with a first surface and a second surface that are opposite each other, and the first surface of the transfer layer clings to the first surface of the three-dimensional mask;
    a pigment layer, attached to the second surface of the transfer layer; and
    a cosmetics machine, wherein when the three-dimensional mask is disposed in the cosmetics machine, the cosmetics machine applies at least one makeup product to the second surface of the transfer layer according to a pre-determined pattern, and the pigment layer with the pre-determined pattern is made of the at least one makeup product applied by the cosmetics machine on the second surface of the transfer layer.

2. The makeup application component according to claim 1, wherein the transfer layer comprises:
    a facial mask, wherein the pigment layer is attached to one surface of the facial mask; and
    an adhesive layer, located between the three-dimensional mask and the facial mask, to bond another surface of the facial mask and the first surface of the three-dimensional mask.

3. The makeup application component according to claim 2, further comprising:
    multiple first marks, disposed on the first surface of the three-dimensional mask; and
    multiple second marks, corresponding to these first marks respectively, and disposed on the another surface of the facial mask.

4. The makeup application component according to claim 1, wherein the transfer layer comprises:
    a facial mask, wherein the pigment layer is attached to one surface of the facial mask;
    a backing, used for supporting the facial mask, wherein one surface of the backing clings to another surface of the facial mask; and
    an adhesive layer, located between the three-dimensional mask and the backing, to bond another surface of the backing and the first surface of the three-dimensional mask.

5. The makeup application component according to claim 4, further comprising:
    multiple first marks, disposed on the first surface of the three-dimensional mask; and
    multiple second marks, corresponding to these first marks respectively, and disposed on the another surface of the backing.

6. The makeup application component according to claim 1, further comprising:
    multiple first marks, disposed on the first surface of the three-dimensional mask; and multiple second marks, corresponding to these first marks respectively, and disposed on the first surface of the transfer layer.

7. The makeup application component according to claim 1, wherein adhesion between the transfer layer and the three-dimensional mask is greater than adhesion between the pigment layer and the transfer layer.

* * * * *